(12) United States Patent
Fink et al.

(10) Patent No.: US 7,918,639 B2
(45) Date of Patent: Apr. 5, 2011

(54) AUTOMATED OBJECT MOVER

(75) Inventors: John Fink, Hamilton (CA); Jonathan David Wittchen, Burlington (CA); Michael P. Riff, Burlington (CA); Gary Darnel, Burlington (CA)

(73) Assignee: Thermo CRS Ltd., Burlington (CA)

( * ) Notice: Subject to any disclaimer, the term of this patent is extended or adjusted under 35 U.S.C. 154(b) by 357 days.

(21) Appl. No.: 12/153,118

(22) Filed: May 14, 2008

(65) Prior Publication Data
US 2008/0286086 A1   Nov. 20, 2008

Related U.S. Application Data

(60) Provisional application No. 60/924,403, filed on May 14, 2007.

(51) Int. Cl.
*B66C 23/00*   (2006.01)
(52) U.S. Cl. ............... 414/744.6; 414/744.3; 414/266
(58) Field of Classification Search ........... 414/744.3, 414/744.6, 266
See application file for complete search history.

(56) References Cited

U.S. PATENT DOCUMENTS

| | | | |
|---|---|---|---|
| 3,985,238 A | 10/1976 | Nakura et al. | |
| 4,507,046 A | 3/1985 | Sugimoto et al. | |
| 4,588,346 A * | 5/1986 | Smith | 414/673 |
| 4,652,204 A | 3/1987 | Arnett | |
| 4,659,278 A * | 4/1987 | Doege et al. | 414/680 |
| 4,909,701 A | 3/1990 | Hardegen et al. | |
| 6,889,119 B2 | 5/2005 | Riff et al. | |
| 7,013,198 B2 | 3/2006 | Haas | |
| 7,096,091 B2 | 8/2006 | Haas et al. | |
| 7,387,485 B2 * | 6/2008 | Dickey et al. | 414/277 |
| 2008/0044261 A1 * | 2/2008 | Neeper et al. | 414/266 |

FOREIGN PATENT DOCUMENTS

| JP | 1228787 A | 9/1989 |
|---|---|---|
| JP | 2004090186 | * 3/2004 |

* cited by examiner

*Primary Examiner* — Donald Underwood
(74) *Attorney, Agent, or Firm* — Baker & Hostetler LLP

(57) ABSTRACT

An automation apparatus and method includes a first unit rotationally moving objects from one area to another, and a second unit connected to the first unit and holding the objects, moving through or offset from the body of the first unit from a first side of the first unit to the other side the first unit in a direction other than the rotational movement by the first unit. Moreover, the apparatus and method provides moving the objects through a vertical axis of the body of the first unit.

19 Claims, 12 Drawing Sheets

AUTOMATED OBJECT MOVER

CROSS-REFERENCE TO RELATED APPLICATIONS

This application claims priority to the provisional U.S. patent application entitled, Automated Object Mover, filed May 14, 2007, having a Ser. No. 60/924,403, the disclosure of which is hereby incorporated by reference in its entirety.

FIELD OF THE INVENTION

The present invention relates generally to an automation system. More particularly, the present invention relates to an automation system with a robotic arm.

BACKGROUND OF THE INVENTION

Scientists have been using robotics and automation to solve problems in research, for example sample processing. Using robotics in automated sample handling is important because of sterility requirements and needs for efficiency. Miniaturization of components have also increased the need for automated sample handling as it is difficult for a researcher to manage small sample sizes in large quantities. Therefore, higher sample density storage is also a problem along with smaller sample volumes. When dealing with miniaturized and small sample volumes, it is difficult for researchers to efficiently manage and still maintain a sterile atmosphere.

In laboratories and other research facilities, microplates are used as a storage medium for samples used in analysis. In a system of a laboratory, many samples are required to be handled. A large quantity of microplates are stored in a single area for handling by automated devices such as a robotic system. An arm of the robotic system is used to move samples from one area to another.

Related robot devices and techniques include for example, U.S. Pat. No. 6,889,119 for ROBOTIC DEVICE FOR LOADING LABORATORY INSTRUMENTS by Riff, et. al., U.S. Pat. No. 7,096,091 for MODULAR ROBOTIC SYSTEM AND METHOD FOR SAMPLE PROCESSING by Haas, et al., and U.S. Pat. No. 7,013,198 for ROBOTIC CAROUSEL WORKSTATION by Haas, which are incorporated herein by reference.

However, the efficiency or throughput of such systems have been limited and also current systems take a large space in order to function to move samples from one area to another. The increased motion and size of such robotic systems, increase costs of the mechanism and thus reduce reliability. There is a need for increasing efficiency in the robotic systems, where they perform functions at a faster throughput and yet be reliable in the activities that they perform.

SUMMARY OF THE INVENTION

The present invention provides a technique and apparatus for faster and more efficient movement of samples, such as microplates from one instrument to another.

The present invention also provides a technique and apparatus for reducing the footprint of the apparatus for automated movement of samples, while economizing the motions of the samples, through minimizing the cost of the mechanism, while increasing reliability.

The automation system of the present invention includes a first unit rotationally moving objects from one area to another, and a second unit connected to the first unit and holding the objects, moving through the body of the first unit from a first side of the first unit to the other side the first unit in a direction other than the rotational movement by the first unit.

The second unit can also be configurable to telescope from and to a location to hold the object or release the object. The second unit can also configurable to reorient the object. There can also be included a pedestal upon which the first unit is based and rotates around, the pedestal providing a base for balancing the first and second unit.

There can also be a pedestal plate being stationary when the first unit rotates about the pedestal, accommodating a reorientation of the object when the second unit moves through or offset from the body. The automation apparatus can also include a counter weight on the second unit providing balance when moving through or offset form the body of the first unit. There can also be a counter weight in the first unit providing balance when moving through or offset from the body of the first unit.

There can also the first unit being a base column having rotational movement, the second unit being an arm for vertical and horizontal movement of the object, and the first unit comprising a frame encasing the first unit with a cavity in between for movement of the second unit through the body of the first unit. The second unit can include an arm for horizontal and vertical motion about the first unit, a gripper connected to the arm for grasping and releasing the object, the gripper configurable for rotational motion about its axis, accommodating reorientation or placement of the object, and a motor accommodating the movement of the arm and gripper with a counter weight providing balance.

In another aspect of the disclosure, a method of an automation system, includes rotationally moving objects from one area to another by a first unit, and holding the objects by a second unit connected to the first unit, and moving through or offset from the body of the first unit from a first side of the first unit to the other side of the first unit in a direction other than the rotational movement by the first unit. There can also be a moving of the objects through a vertical axis of the body of the first unit.

In another aspect of the disclosure, an automation system, includes a first means rotationally moving objects from one area to another, and a second means connected to the first means and holding the objects, and moving through or offset from the body of the first means from a first side of the first means to the other side the first means in a direction other than the rotational movement by the first means.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art can appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
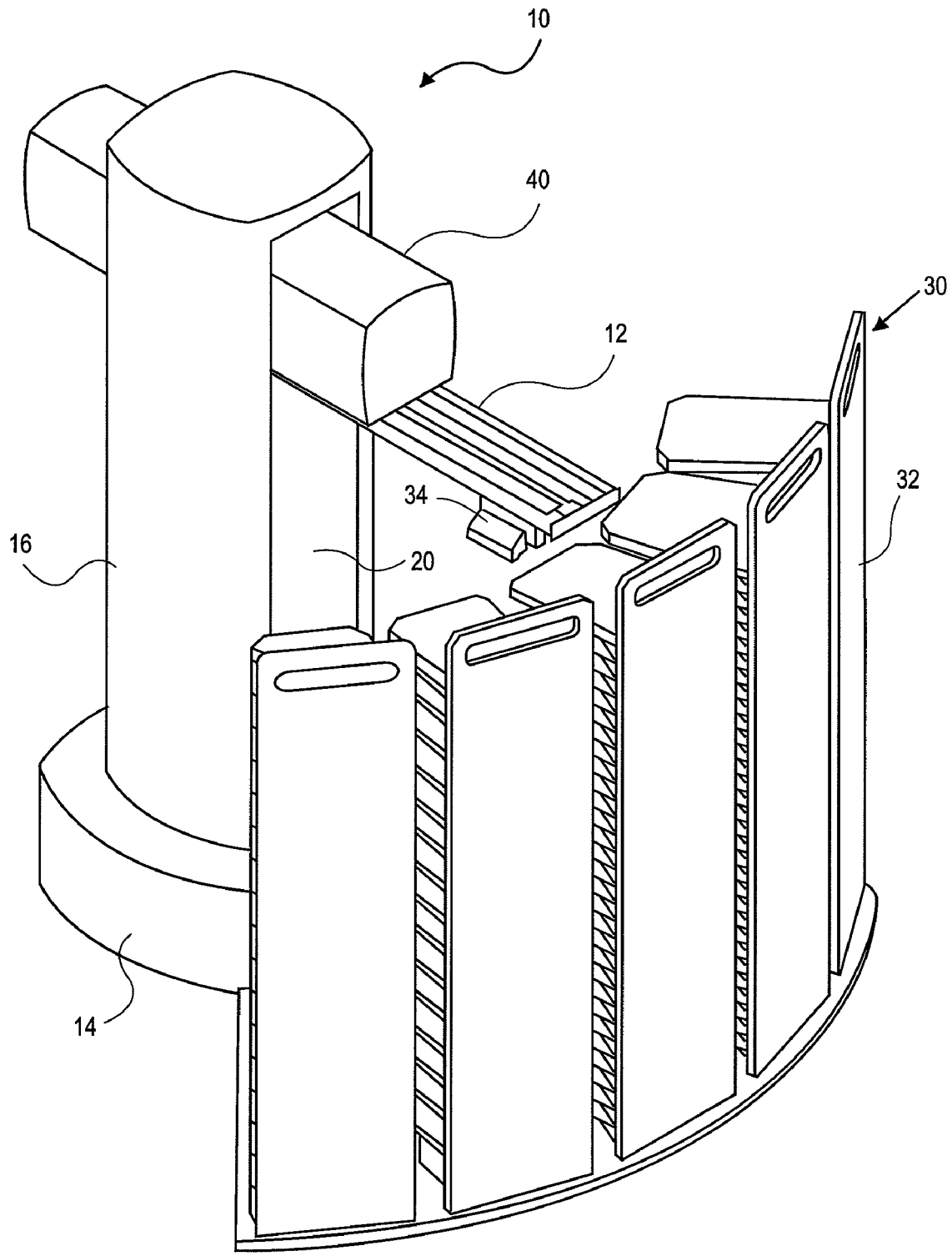
FIG. 1 is a cylindrical plate mover robot according to an embodiment of the disclosure.

In one embodiment of the present invention, a cylindrical plate mover robot 10 is shown in FIG. 1. The storage unit 30 includes a plurality of hotels 32 for storage of microplates. The robot 10 moves its arm 12 in order to move between the storage areas of the hotels 32 in order to transfer the microplates 36. The hotels 32 with shelves are located radially around the robot 10. The hotels 32, located radially around the robot, can be with or without shelves. The objects can be stacked in the hotels 32 without the shelves, or be placed within the hotels 32 with shelves.

Figure 2:
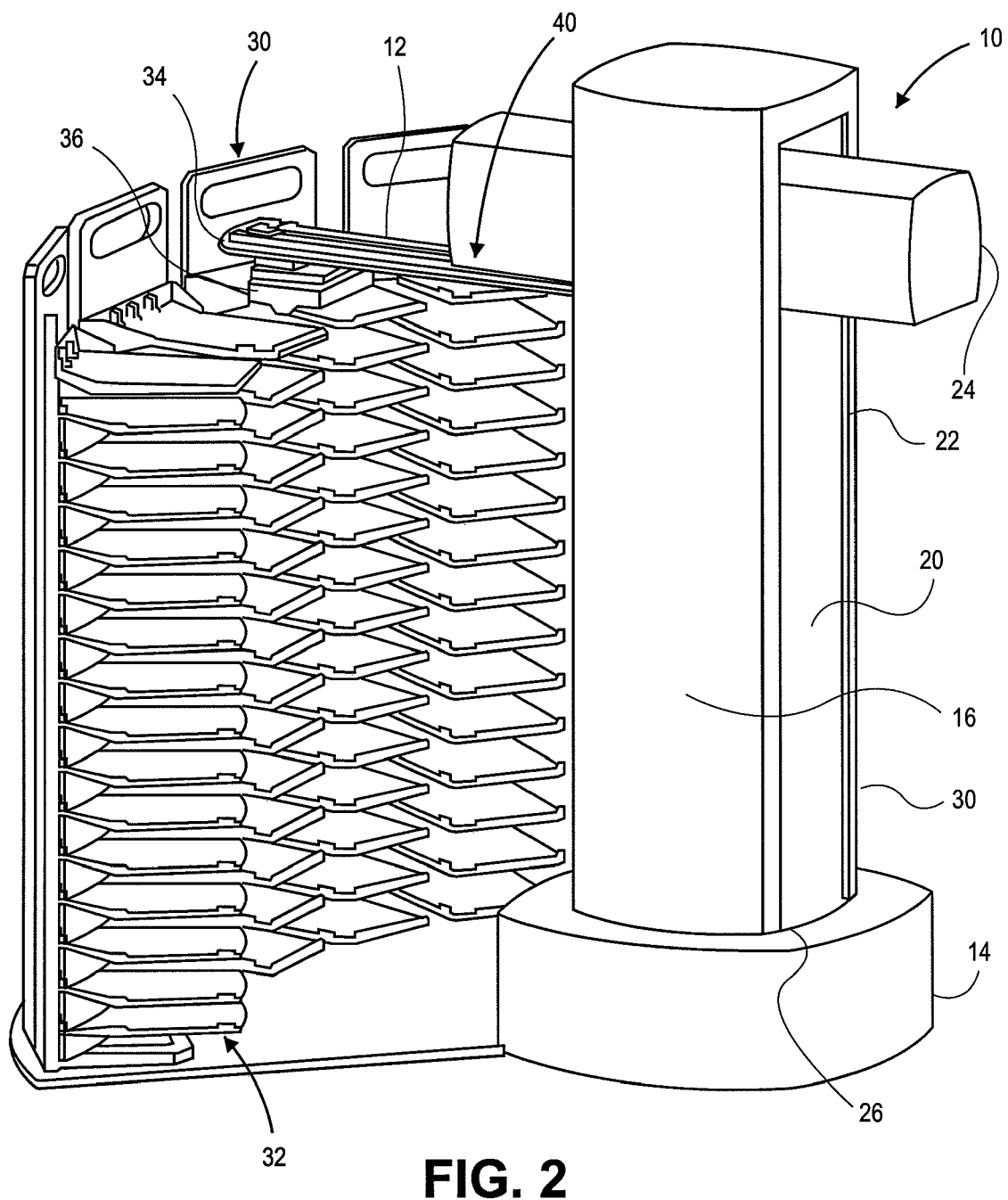
FIG. 2 is another detailed view of the apparatus of FIG. 1 for moving plates.

Referring to FIGS. 1 and 2, the robot 10 is secured through a pedestal unit 14. The pedestal unit 14 is connected to a vertical extension or base column 16. The rotational movement of the base column 16 can be carried out through a gearbox and servo motor housed within the robot 10. Any of the motors can be for example a stepper or a servo motor. Furthermore, movement of the arm 12 can be accommodated by another motor and a set of gears. A plurality of motors can be used for the different motions of the robot 10 which can be housed within the robot 10. For example, one motor can be used for the rotational movement of the base column 16, a second motor for the vertical movement of arm 40, a third motor for the horizontal movement of the arm 40, a fourth motor for movements by the gripper 34 and a fifth motor for possibly rotating the gripper 34.

Instead of a cylindrical design where a cylindrical robot 10 has (a) a revolute base joint and (b) a translational vertical axis and (c) either a translational radial extension (offset from the vertical axis or biased to work on one side of the vertical axis) or a pair of revolute joints intended to provide a radial displacement of the payload (seen in SCARA (Selective Compliant Assembly Robot Arm or Selective Compliant Articulated Robot Arm) robots), the present invention allows a translational radial axis to work on the centerline of the revolute base joint, and allows the translational radial axis to extend through the centerline of the base rotation and deliver the payload through the centerline of the vertical axis. The delivery of the payload can also be offset from the centerline of the vertical axis. Such an arrangement provides fast motion of the payload from one side of the base rotation to the other, thereby economizing the motion of the revolute base joint. Also, the present invention allows the footprint of the mechanism to be smaller because the payload can be held in a position above the centerline of the vertical axis for vertical motion between source and destination where traditional mechanisms must accommodate a position of the payload offset from the vertical axis, which usually results in an appreciable loss of available space for instrumentation (an annular cross section when viewed from the vertical).

The present invention moves plates faster and more efficiently since the robot 10 does not have to rotate +/−180 degrees to reach 360 degrees the gripper can now travel through the body of the robot through walls 22 within the body of the base column 16, creating a chamber 20 to access an instrument on the other side. The revolute base joint 26 (and the base column 16) can only have to rotate +/−90 degrees in most cases. The arm 12 can pick up the microplate 36 through a gripper 34 and move through the chamber 20 to the other side the base column 16 of the robot 10, where the arm 12 is supported by the T-portion or the arm support 24. The T-portion or the arm support 24 is fixed to and stationary relative to the base column 16.

The difference is the telescoping arm 12 that travels through the body of the robot 10, via the chamber 20, eliminates the need to rotate when accessing an opposite positioned instrument and/or rotates less to reach an instrument greater than 90 degrees to either side of the robot 10.

The telescoping arm 12 is included in the present invention rather than just rotating around the robot base as the present invention actually moves through the base column 16 as well as rotates. This enables the robot 10 to rotate less and move microplates 36 from one side to the other more quickly and efficiently.

Figure 3:
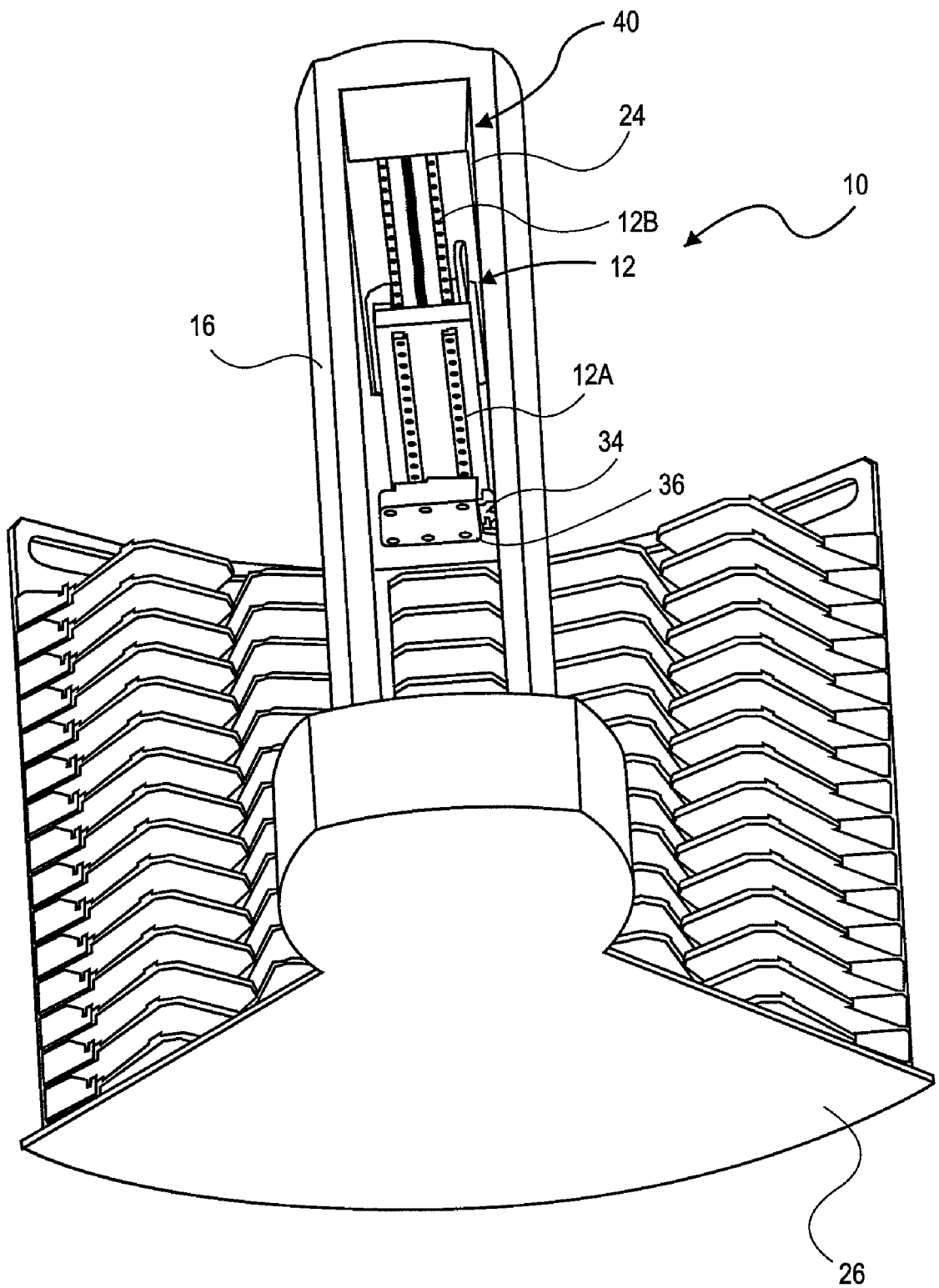
FIG. 3 is view of the arm portion of the plate mover robot.

Referring to FIG. 3, a prospective view of the robot 10 is shown detailing an example of the arm 40 and the movement through the chamber 20 of the base column 16. The arm 40 includes a support portion 24 that supports the movement of the telescoping arm portion 12 which includes a first part 12A and a second part 12B.

Figure 4:
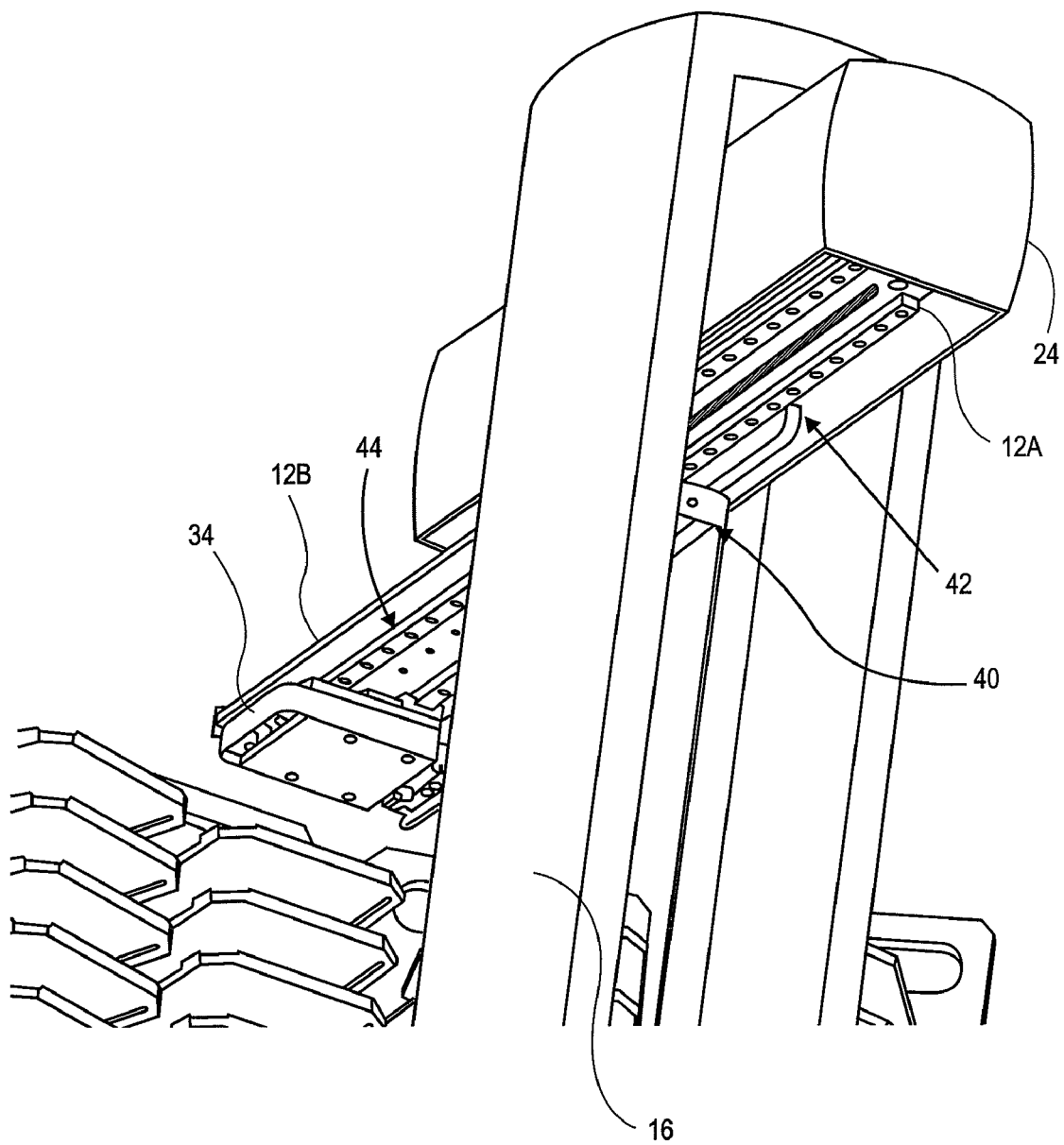
FIG. 4 is a close-up view of the arm portion of the plate mover robot of FIG. 3.

A close-up view of the telescoping arm 12 is shown in more detail in FIG. 4. The first part of the telescoping arm 12A is attached to the support portion 24. The first part 12A includes a plurality of glides 42 accommodating movement approximately perpendicular to the base column 16, by the second part 12B of the telescoping arm 12. Other types of components can be used other than glides 42 to accommodate the movement of the telescoping arm 12. The angle between the arm 40 and the base column 16 can be any angle. For example, the angle can be about 90 degrees between the arm 40 and base column 16. The second part 12B of the telescoping arm 12 moves along the glide 42 on the first part 12A of the telescoping arm 12. In addition, the gripper 34 moves along the glide 44 on the second part 12B of the telescoping arm 12, thus accommodating a movement of the microplate or object 36 through the chamber 20 of the body of the base column 16. The gripper 34, also can incorporate a rotational movement accommodating a reorientation of the plate or object 38, after the gripper 34 moves to the other side of the base column 16. Another motor and gearbox can accommodate the motion of the telescoping arm 12.

Figure 5:
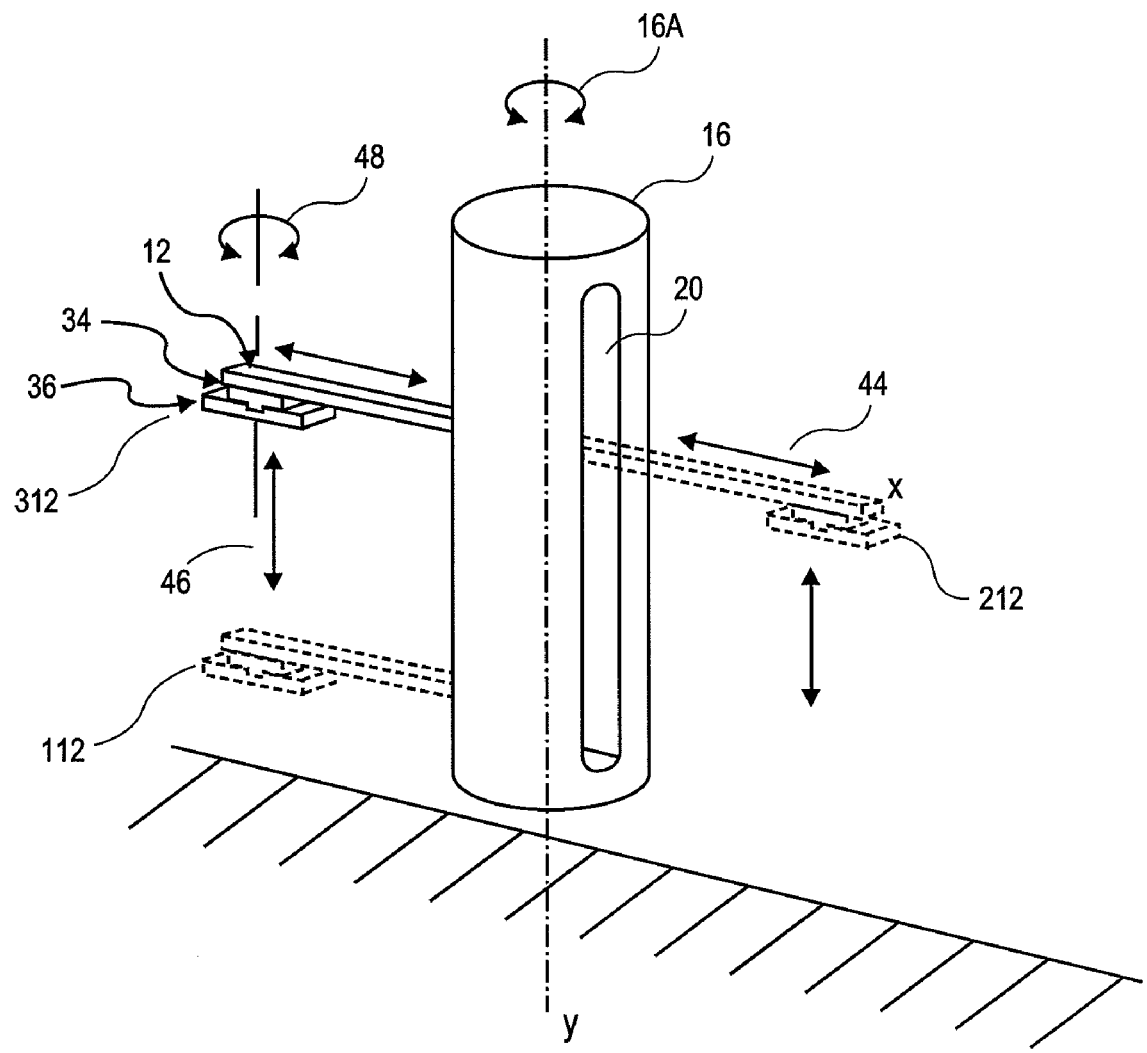
FIG. 5 is a view of the motion of the robot.

Referring to FIG. 5, the base column 16 can rotate along a y-axis, to accommodate the gripper 34 to seize the microplates 36 or other objects and move to another storage area. The telescoping arm 12 can move along the x-axis as shown by movement 44, from one side of the base column 16 to the other side as shown by position 212. The telescoping arm 12 can also move along the y-axis as shown by movement 46 to position 112, or other area along the length of the chamber 20.

The gripper portion 34 of the telescoping arm 12 can also rotate about the y-axis as shown in movement 48, in order to reorient the microplate or object 36 held by the gripper portion 34, when moving from position 312 to position 212 through the base column 16 of the robot 10.

Other embodiments are included that can move the gripper from one side of the robot 10 to the other side, by moving through the body of the robot 10 itself rather than rotating around the body to reach the objects 36. For example, the telescoping arm 12 could move through a different type of motion to get from position 312 to position 212. The chamber 20 can be a different shape to accommodate the motion of the gripper 34 and the telescoping arm 12. The telescoping arm 12 can also include different parts other than a first part 12A and the second part 12B, and the associated glides. The movement of the telescoping arm is not limited to a direction along the x-axis, but could be any type of movement as long as the telescoping arm can be on the other side of the base column. The shape of the base column 16, does not have to be a column, but can be any shape protruding from the pedestal unit 14. The pedestal unit 14 can also be removed, and the robot can include only the base column 16 that is fastened to a work area.

The telescoping arm 12 connected to the base column 16 and holding the objects 36, moves through the body of the base column 16 from a first side of the base column 16 to the other side the base column in a direction other than the rotational movement by the base column 16.

The robot 10 can reorient the microplate or object 36 in a number of different manners other than rotating the microplate. In an alternative embodiment, the arm 40 of the robot 10 can set down the microplate or object 36, and then while it is set down, then rotate the plate. Then the gripper 34 can pick the object 36 back up quickly in a different orientation, rather than rotating it within the gripper 34.

In general as seen in FIGS. 1 through 5, the robot can be a cylindrical plate moving robot, but other configurations can be used. The base column 16 moves rotationally. The arm 40 travels vertically up and down the base column. The gripper 34 can rotate to reorient the plate, or set down and then reorient the plate 36. The hotels or plate feeders 32 can be used for the storage of the microplates 36, but other types of storage for the objects 36 can be used. The telescoping arm 12 with the plate gripper 34 can be used to grasp the objects 36. The gripper 34 travels through the tower (base column 16) of the plate mover. This movement through the body of the robot 10 accommodates a very fast plate delivery from one side to the other. Therefore, a movement through the body of the robot allows for less column base 16 rotation to reach 360 degrees.

A variety of different motions and movements of the arm 40 can be used to accommodate the movement through the body of the robot 10.

Figure 6:
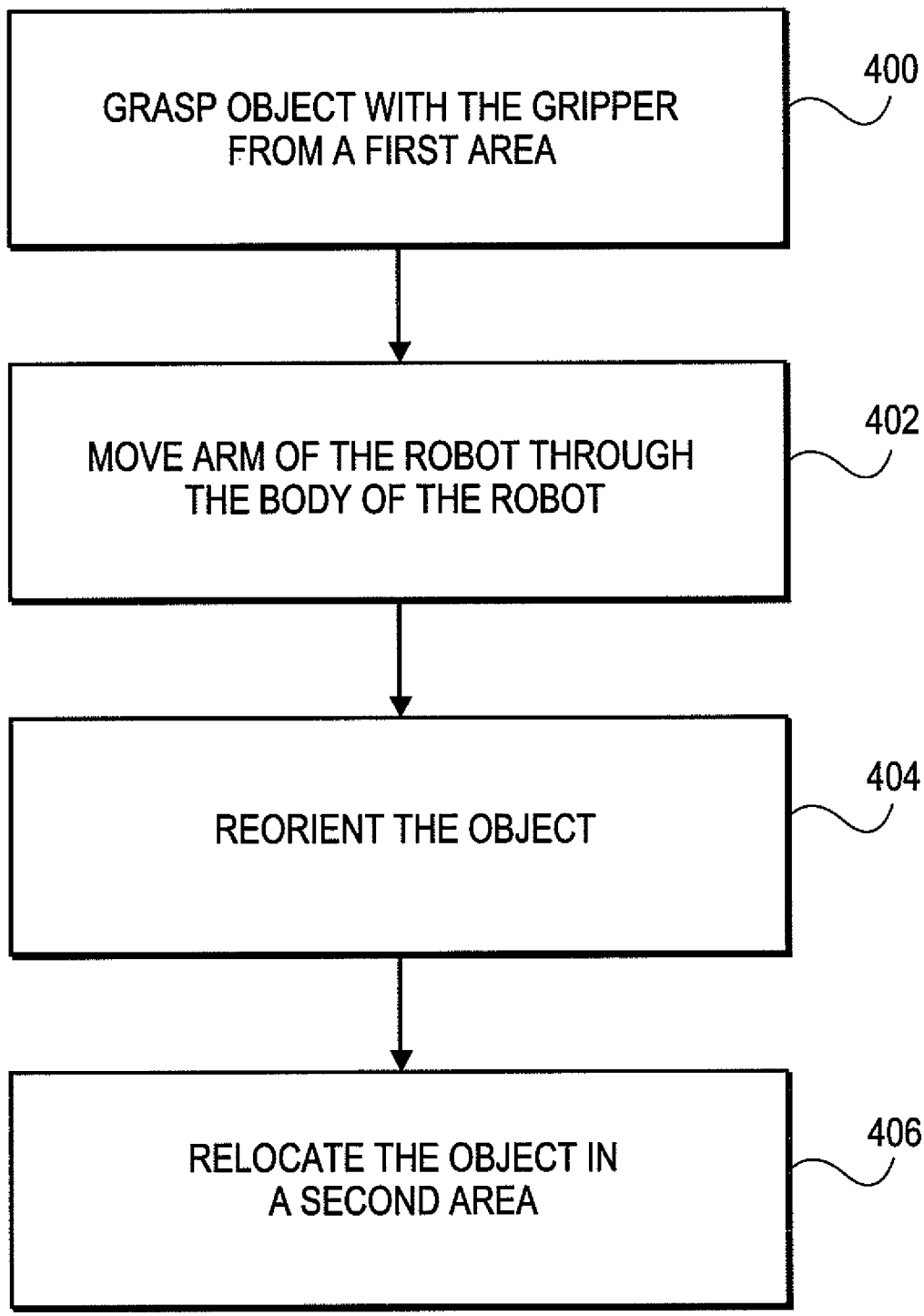
FIG. 6 is a flow diagram of the technique of the present disclosure.

Referring to FIG. 6, the technique for moving the objects from one area to another can be shown by the following. First, the gripper 34 picks up the object from a first area, such as from a shelf from one of the hotels 32 (step 400). Secondly, the telescoping arm 12 portion of the arm 40 moves through the body of robot 10 to move the object 36 to the other side of the robot 10 (Step 402). For example, the telescoping arm 12 goes through the chamber 20 in the base column 16 and moves the object to the other side. The telescoping arm 12 can then move vertically, up or down to position the object, or rotate about the Y-axis to further position the object at a certain shelf of another hotel.

The gripper 34 can then reorient the object 36, by for example, rotating the gripper or placing down and reorienting the object 36. Then, the gripper 34 relocates the object in a second area, such as another shelf in one of the hotels 32.

The robot 10 can be instructed to go through the body, if a certain condition exists. For example, if it is faster for the robot to have the arm go through the body when having to move the object a certain rotational angle, then the robot will go through the body. For example, if the rotation needed is in excess of 90 degrees, then the arm 40 will go through the body of the robot 10, or if the movement necessary is a certain amount of degrees less than 180.

Figure 7A:
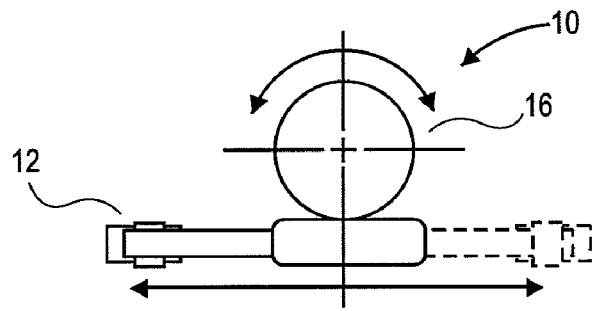
FIG. 7A is a top view of the arm portion of the plate mover robot, moving offset from the center axis.
Figure 7B:
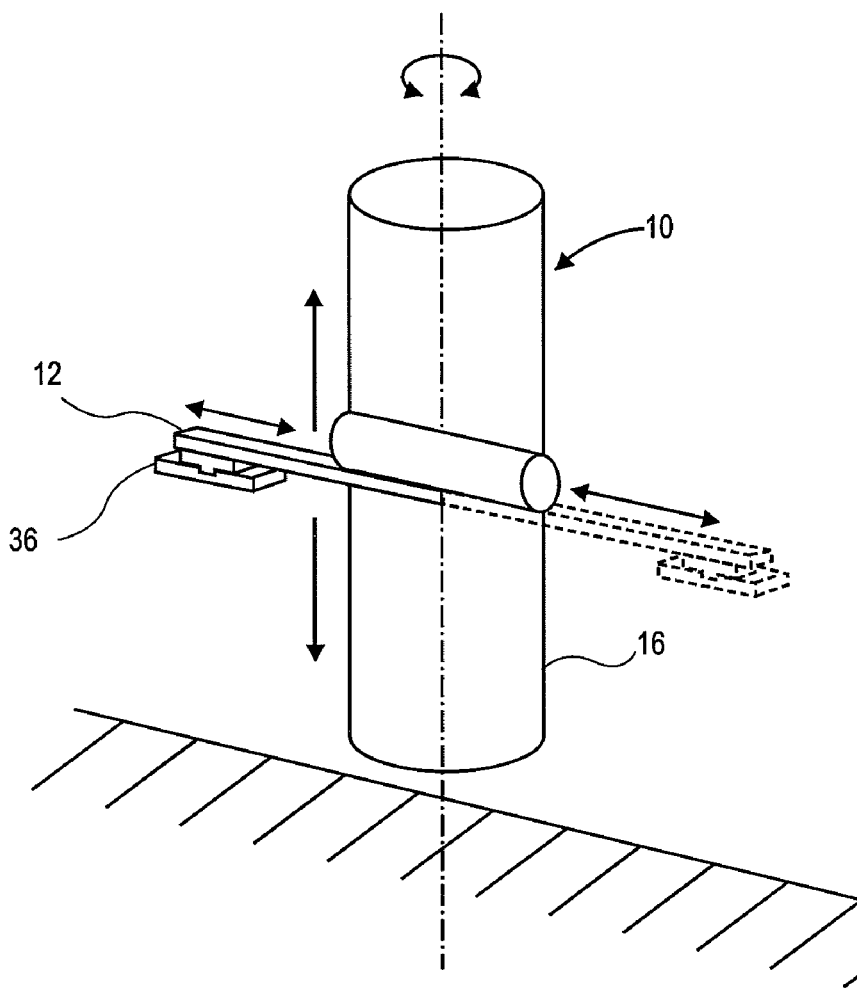
FIG. 7B is a side view of the arm portion of the plate mover robot of FIG. 7A.

Referring to FIGS. 7A and 7B, in another embodiment, the arm 12 can also move beside the body, rather than through the body of the robot 10, which also achieves the benefit of efficiency as when the arm is along the center axis. The arm does not have to move through the body of the robot 10, but can be actually going through the side of the base column 16 as seen in FIGS. 7A and 7B.

Figure 8:
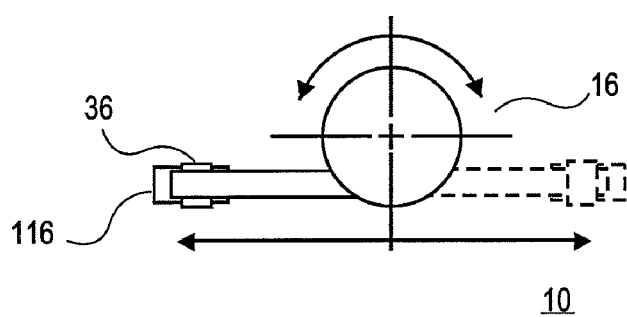
FIG. 8 illustrates another embodiment of the robot of the present disclosure.

Referring to FIG. 8, in another embodiment, the arm 116 is offset from the center axis Y, which also achieves the benefit of efficiency as when the arm is along the center axis. Furthermore, the arm 116 can be not telescoping, but the object 36 or payload, such as a microplate, travels along a track or rail from one side of the robot to the other and still go through to the other side of base column 16 of the robot 10.

The present invention can be realized as computer-executable instructions in computer-readable media. The computer-readable media includes all possible kinds of media in which computer-readable data is stored or included or can include any type of data that can be read by a computer or a processing unit. The computer-readable media include for example and not limited to storing media, such as magnetic storing media (e.g., ROMs, floppy disks, hard disk, and the like), optical reading media (e.g., CD-ROMs (compact disc-read-only memory), DVDs (digital versatile discs), re-writable versions of the optical discs, and the like), hybrid magnetic optical disks, organic disks, system memory (read-only memory, random access memory), non-volatile memory such as flash memory or any other volatile or non-volatile memory, other semiconductor media, electronic media, electromagnetic media, infrared, and other communication media such as carrier waves (e.g., transmission via the Internet or another computer). Communication media generally embodies computer-readable instructions, data structures, program modules or other data in a modulated signal such as the carrier waves or other transportable mechanism including any information delivery media. Computer-readable media such as communication media may include wireless media such as radio frequency, infrared microwaves, and wired media such as a wired network. Also, the computer-readable media can store and execute computer-readable codes that are distributed in computers connected via a network. The computer-readable medium also includes cooperating or interconnected computer readable media that are in the processing system or are distributed among multiple processing systems that may be local or remote to the processing system. The present invention can include the computer-readable medium having stored thereon a data structure including a plurality of fields containing data representing the techniques of the present invention.

Figure 9:
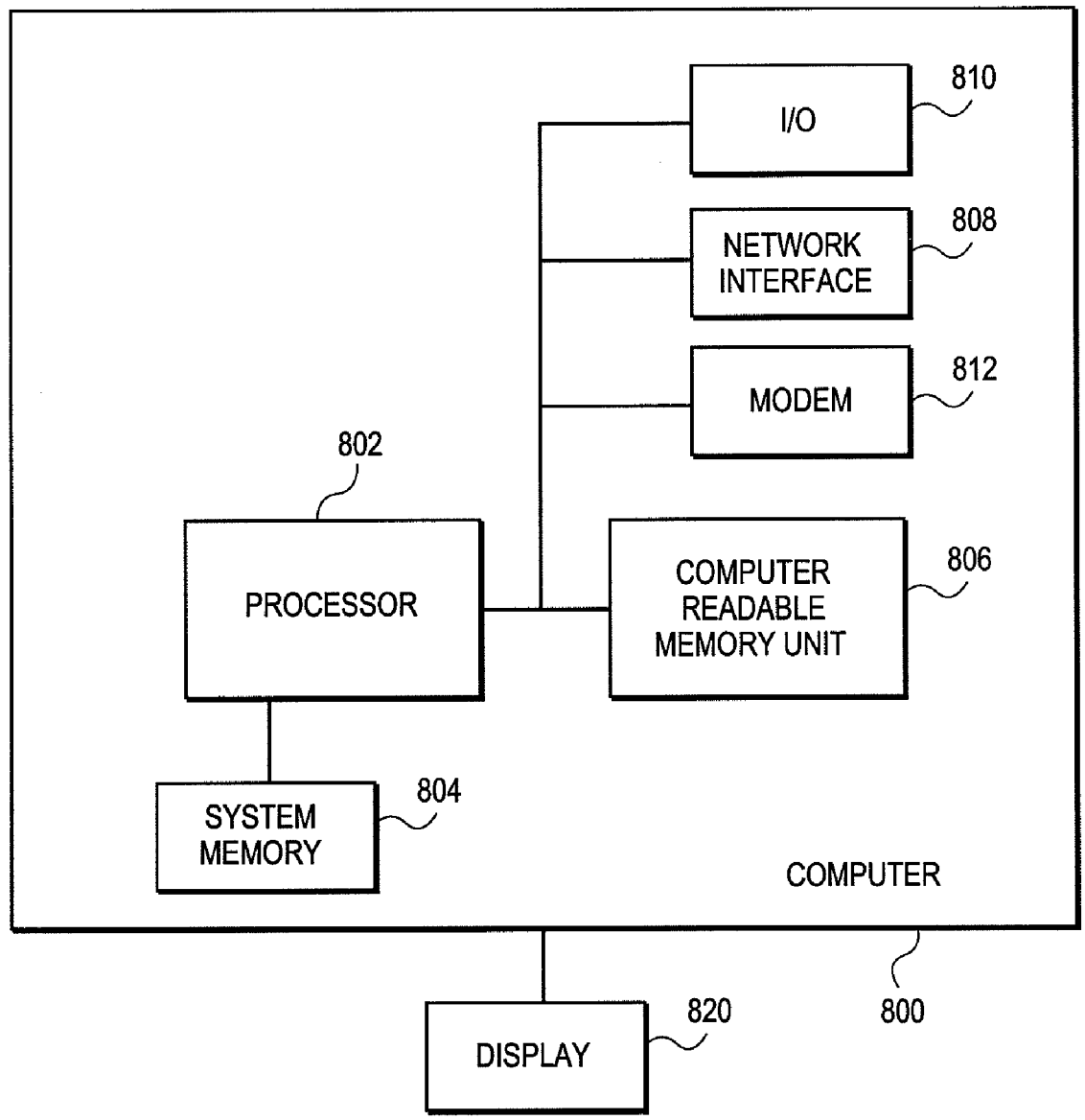
FIG. 9 is an example of a computer that accommodates the computer executable instructions of the present disclosure.

Referring to FIG. 9, an example of a computer 10, but not limited to this example of the computer, that can read computer readable media that includes computer-executable instructions of the present invention includes a processor 802 that controls the computer. The processor 802 uses the system memory 804 and a computer readable memory device 806 that includes certain computer readable recording media. A system bus connects the processor 802 to a network interface 808, modem 812 or other interface that accommodates a connection to another computer or network such as the Internet. The system bus may also include an input and output interface 810 that accommodates connection to a variety of other devices. The output of the computer 800 can be shown on the display 820 connected to the computer 800.

A variety of different configurations are possible that accommodate the arm to go through the body of the robot in order to move the object held by the arm from one area to another. The above is shown only as an example of such a structure accommodating such a movement by the robot 10.

Figure 10:
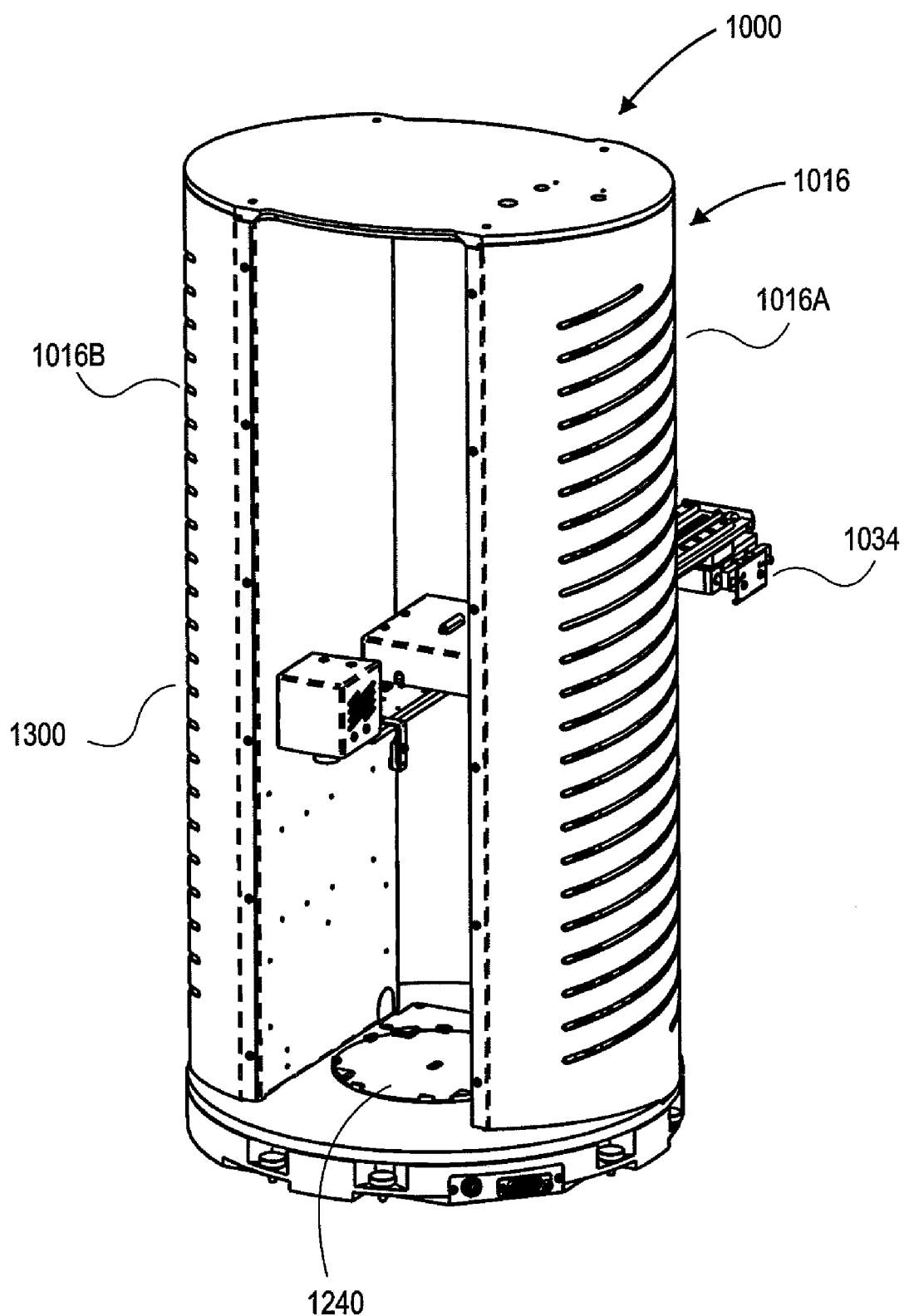
FIG. 10 is a view of a robot of another embodiment of the present disclosure.
Figure 11:
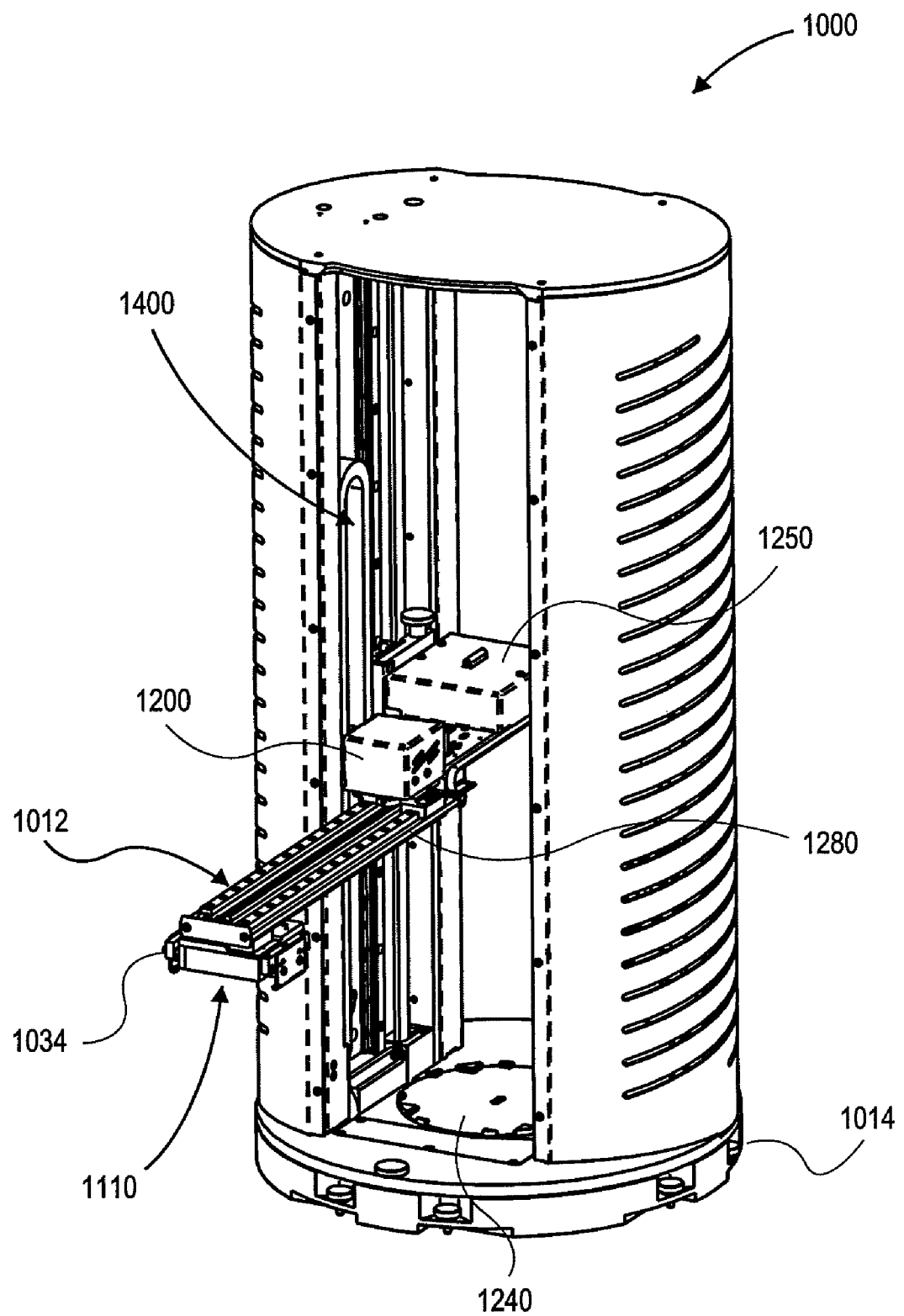
FIG. 11 is another view of a motion of the robot of FIG. 10.
Figure 12:
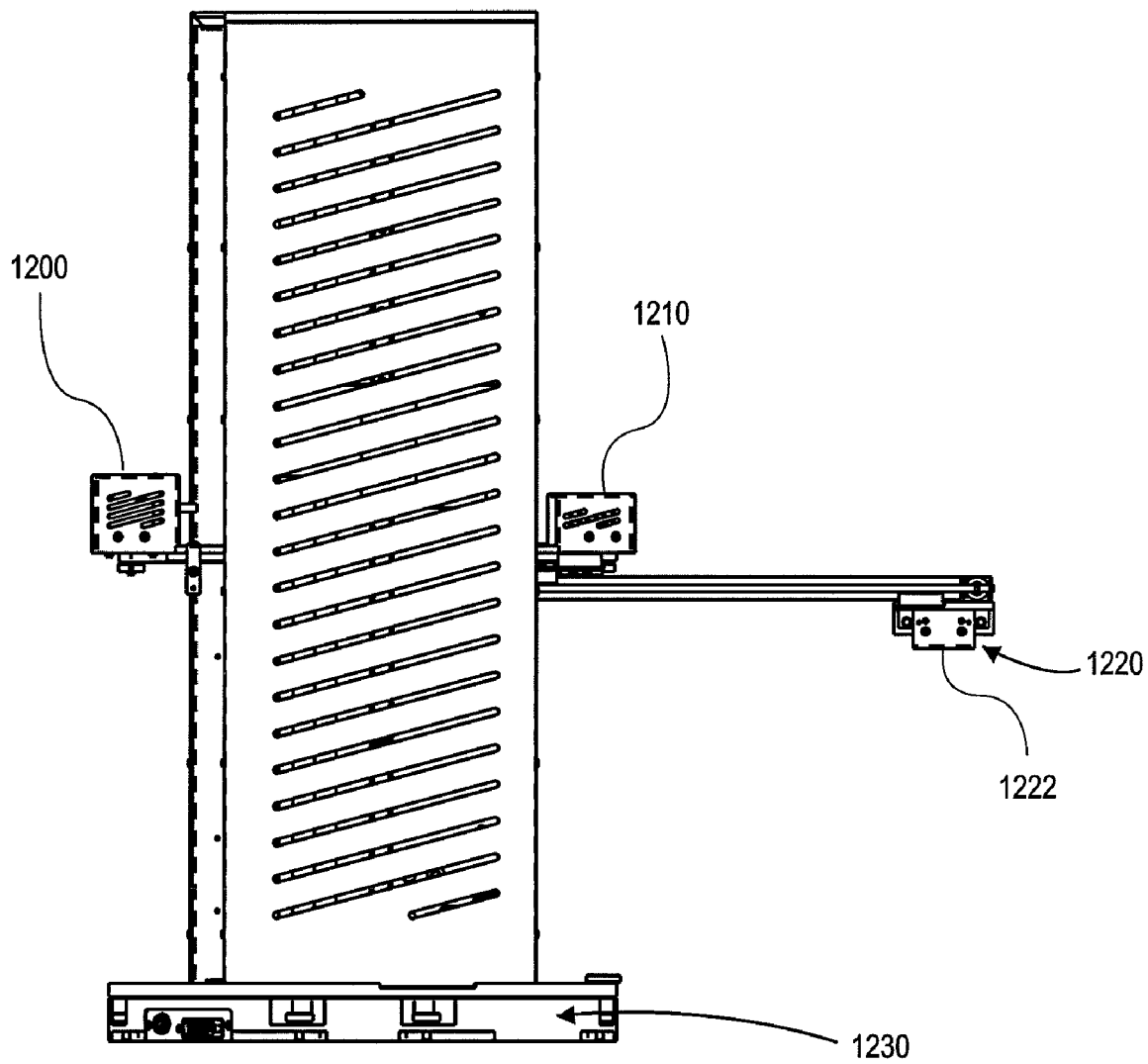
FIG. 12 is a side view of the robot of FIG. 10 as the gripper and arm move through the body.

Referring to FIGS. 10-12, an alternative embodiment of the robot 1000 is shown with alternative views and motion. As seen in FIG. 10, the gripper 1034 is on one side and then in FIG. 11, the motion of the arm 1012 shows that it goes through the body to the other side of the column 1016. The column 1016 also has panels 1016A and 1016B encasing the arm 1012 structure with a cavity in between accommodating the passage of the gripper 1034 from one side of the robot 1000 to the other. The circuit board 1300 for the electronic system of robot 1000 can be on the left side door 1016B, or alternatively on the other side or another location. The pedestal 1014 can include motors 1230 for movement of the column 1016. The pedestal 1014 can alternatively include motors for other types of movement of the robot 1000 including the arm 1012 or other part.

A plate or object held by the gripper 1034 can be reoriented in manner separate from that mentioned earlier. In order to rotate the plate, the gripper can set the plate down inside the cavity of the robot 1000 between sides 1016A and 1016B of the column 1016, on top of base surface of pedestal plate 1240. The pedestal plate 1240 can be configured to not rotate as the base column 1016 rotates. Therefore, when the arm 1012 rotates around with the base column 1016, the pedestal plate 1240 stays stationary. The robot 1000 then rotates around the object 36, such as a plate, where the pedestal plate 1240 stays stationary, and the gripper 1034 then picks up the plate in the adjacent or opposite orientation. This internal nest of the pedestal plate 1240 of the robot 1000 provides the base for reorienting the plate or object being moved.

Alternatively, a separate external device can also be used to reorient the plates. The separate device can be used by the gripper 1034 to position the object 36 on the plate and the separate device can reorient the object 36, and then once the object reoriented in the direction needed, the gripper 1034 can pick the object up again for storage on the hotels 32 of the storage unit 30. The reorientation can be needed when the object 36 is moved through the body of the robot 1000.

Alternatively, the reorientation can also be made by the gripper 1034 itself by a rotation or other movement of the gripper 1034. Additional means of reorienting the objects 36 can also be utilized.

The robot 1000 can be balanced in a variety of ways when it is stationary and when it is moving, including movement through or alternatively, offset from the body of the robot 1000. Balancing mechanisms or counter-weights can be placed in the arm 1034, the column 1016 and/or the pedestal 1014 or base of the robot 1000.

As seen in FIG. 10, as the gripper 1034 travels vertically through the column 1016, a counter-weight can be used in one side of the column 1016A and/or the other 1016B. Additionally, as the gripper 1034 moves horizontally through the body of column 1016, the arm 1012 as seen in FIG. 11, can include a counter weight. The counter weight can be included in first block unit 1200 or other area such as second block 1210 or nothing can be added to the second block 1210.

The first block unit 1200 can also include the motor encoder for movement of the arm 1012, for example, in the in an out motion along the R-axis. The motors in the pedestal 1230 (or alternatively in other areas of the robot 1000) can include the up and down motion in the Z-axis. Additional parts or means 1400 accommodating the motion in the Z-axis can be housed in a side of the column 1016. The motors in the pedestal 1230 (or alternatively in other areas of the robot 1000) can include the rotational motion in the θ-axis (theta). There can also be slip rings underneath the center of the pedestal 1230 area.

As seen in FIGS. 10-12, the arm 1012 can be telescoping to provide a greater flexibility in the movement and reach of the gripper 1034. The gripper 1034 can also include a motor 1220 for the movement of the gripper. The motor can allow for the gripping motion of the gripper 1034 in order to clasp and release the objects 36 or any other motion required by the gripper. Additionally, the gripper motor 1220 or other motor can be configured for rotational movement of the gripper 1034 for reorienting the objects 36.

The second block 1210 can house optional devices while the first block 1200 has the motor encoder. The location of the motors, controllers and other devices for motion can be housed in other locations and this is given only as an example.

A sensor 1222 can be attached to the gripper 1034 in order to sense the objects 36 for the gripper 1034. The sensor 1222 can be located on the bottom of the gripper 1034, for example, but is not limited to this location. The sensor can be an optical sensor or other type of sensor for sensing objects 36 and/or the movement of the gripper 1034. Additional sensors can also be mounted providing feedback to the control system of the robot 1000. The sensor 1222 can be located to provide feedback that the gripper 1034 is getting close to the plate or object 36. An external controller or computer can be used to control the robot 1000 and its movement, or the controller or processor for control can be housed in the robot 1000. Additionally a predetermined set of instructions can be programmed for movement of the robot 1000 for movement and positioning of the objects.

The gripper 1034 can hold an object such as plate 1110 or other object for movement through the cavity between the walls 1016A and 1016B of the column 1016 for movement of the arm 1012 through the body of the robot 1000. The arm 1012 can move in the theta, R and Z axis for full flexibility of motion of the robot 1000. Additional devices or weight 1250 can be housed in the second block 1210 or nothing additional. The arm 1012 can include additional parts 1280 accommodating the movement in the R axis including for example a belt or other part.

Figure 13:
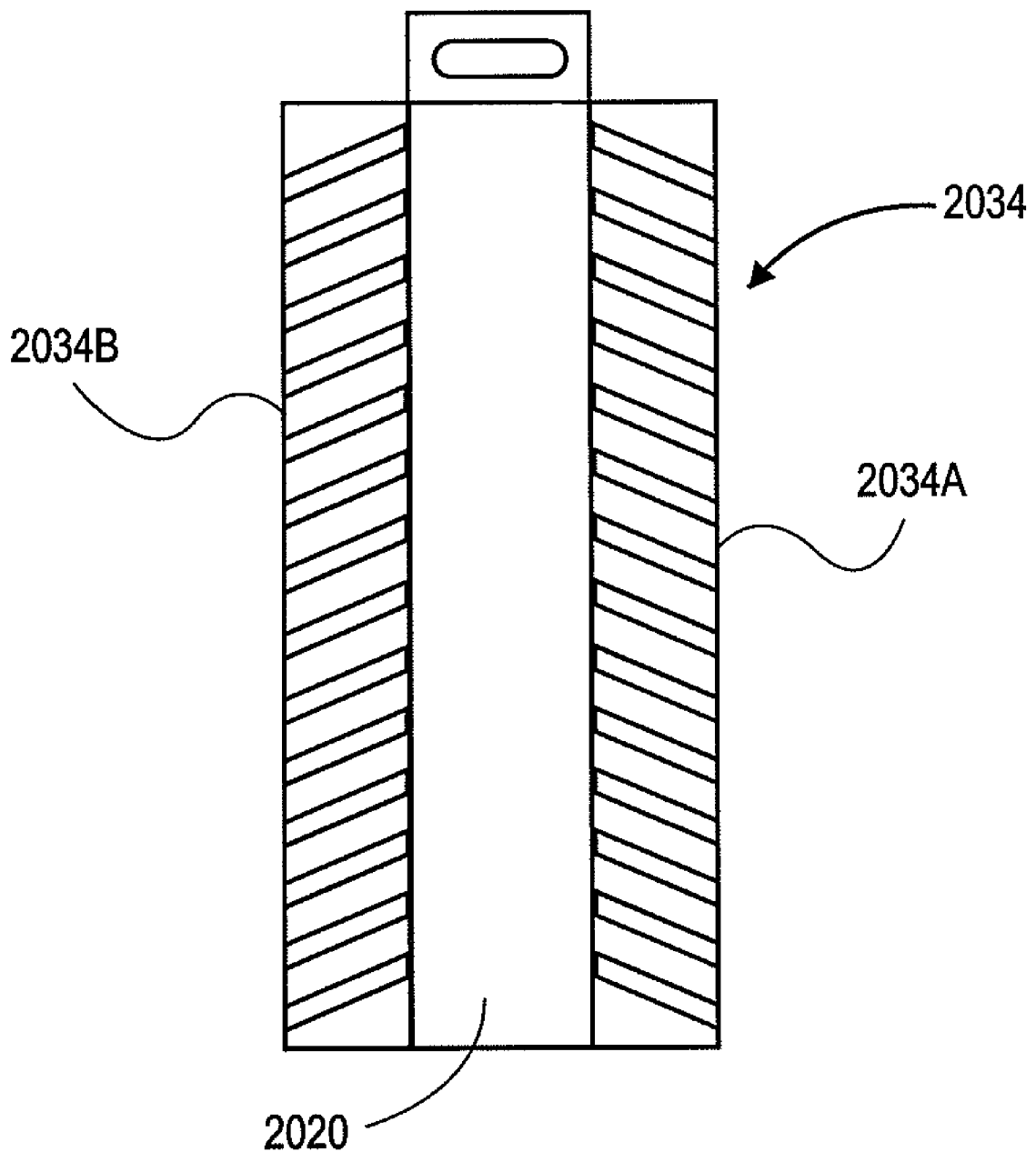
FIG. 13 is a front view the hotel with open doors.

Referring to FIG. 13, additionally the hotel of 32 can be embodied as the hotel 2034 that allows access of the plates or other objects from both sides. FIG. 13 shows the hotel 2034 with the doors 2034B and 2034A in an open position. The access provided by the doors allows for a versatile and flexible access to the plates or other objects 36 stored in the storage area 2020. The doors can be attached to the storage area 2020 in a variety of ways including being hinged or being positioned in a sliding manner to allow both doors 2034A and B to open for access to the plates or objects 36. Different types of balancing measures can also be included to allow for the opening and closing of the doors 2034A and B and different types of fastening means for the doors 2034A and B can also be used. This would allow a more flexible way to access the stacked objects stored in the hotel 2034.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An automation apparatus, comprising:
a first unit, including a body, for moving objects from one area to another;
a second unit, connected to the first unit, for moving the objects through the body of the first unit from one side of the first unit to the other side the first unit; and
a rotating pedestal, upon which the first unit is mounted, including a stationary pedestal plate for accommodating a reorientation of the objects when the objects move through the body of the first unit.

2. The automation apparatus of claim 1, wherein the objects move through a vertical axis of the body of the first unit.

3. The automation apparatus of claim 2, wherein the second unit includes a telescoping portion.

4. The automation apparatus of claim 2, wherein the second unit includes an articulated portion to reorient the object.

5. The automation apparatus of claim 1, further comprising a counter weight on the second unit.

6. The automation apparatus of claim 1, wherein:
the first unit is a base column, having rotational movement, that includes two plates defining a cavity therebetween, and
the second unit is an arm.

7. The automation apparatus of claim 2, wherein the second unit comprises:
an arm;
a rotatable gripper, connected to the arm, for grasping, releasing and reorienting the objects; and
a motor, accommodating the movement of the arm and gripper, with a counter weight providing balance.

8. A method of an automation system, comprising:
moving objects from one area to another using a first unit mounted to a rotating pedestal that includes a stationary pedestal plate;
moving the objects through the first unit from one side of the first unit to the other side of the first unit using a second unit connected to the first unit; and
reorienting the objects, using the second unit and the stationary pedestal plate, when the objects move through the first unit.

9. The method of claim 8, further comprising moving the objects through a vertical axis of the first unit.

10. The method of claim 9, further comprising telescoping the second unit from and to a location to hold the object or release the object.

11. The method of claim 9, wherein the second unit is an arm with an articulated portion.

12. The method of claim 8, further comprising providing a counter weight on the second unit.

13. The method of claim 8, wherein:
the first unit is a base column, having rotational movement, that includes two plates defining a cavity therebetween, and
the second unit is an arm.

14. The method of claim 9, wherein the second unit is an arm, and further comprising:
moving the arm in horizontal and vertical directions about the first unit;
grasping and releasing the objects using a gripper connected to the arm, the gripper accommodating reorientation or placement of the objects; and
providing movement of the arm and gripper through a motor with a counter weight providing balance.

15. An automation system, comprising:
a first means for moving objects from one area to another;
a second means, connected to the first means, for moving the objects through the first means from one side of the first means to the other side the first means; and
a rotating third means, upon which the first means is mounted, including a stationary portion for accommodating a reorientation of the objects when the objects move through the first means.

16. The automation system of claim 15, wherein the objects move through a vertical axis of the first means.

17. The automation system of claim 16, wherein the second means includes a telescoping portion.

18. The automation system of claim 16, wherein the second means includes an articulated portion to reorient the objects from a first direction to a second direction.

19. The automation system of claim 15, wherein the first means includes a pair of walls defining a cavity therebetween through which the object is moved.

* * * * *